US009940266B2

(12) United States Patent
Van Rooyen et al.

(10) Patent No.: US 9,940,266 B2
(45) Date of Patent: Apr. 10, 2018

(54) METHOD AND SYSTEM FOR GENOMIC VISUALIZATION

(71) Applicant: Edico Genome Corporation, La Jolla, CA (US)

(72) Inventors: Pieter Van Rooyen, San Diego, CA (US); Gavin Stone, San Diego, CA (US); Lucian Iancovici, San Diego, CA (US)

(73) Assignee: Edico Genome Corporation, San Diego, CA (US)

( * ) Notice: Subject to any disclaimer, the term of this patent is extended or adjusted under 35 U.S.C. 154(b) by 0 days.

(21) Appl. No.: 15/076,583

(22) Filed: Mar. 21, 2016

(65) Prior Publication Data

US 2016/0283407 A1    Sep. 29, 2016

Related U.S. Application Data

(60) Provisional application No. 62/137,103, filed on Mar. 23, 2015.

(51) Int. Cl.
*G06F 12/14*     (2006.01)
*G06F 19/22*     (2011.01)
(Continued)

(52) U.S. Cl.
CPC .... *G06F 12/1408* (2013.01); *G06F 17/30091* (2013.01); *G06F 19/22* (2013.01);
(Continued)

(58) Field of Classification Search
CPC .. G06F 19/322; G06F 19/324; G06F 12/1408; G06F 17/30091; G06F 19/22; G06F 19/28
(Continued)

(56) References Cited

U.S. PATENT DOCUMENTS 5,859,972 A * 1/1999 Subramaniam ... G06F 17/30569
707/999.003
5,964,072 A   10/1999 Rasmussen
(Continued)

FOREIGN PATENT DOCUMENTS

CN    105051741 A    11/2015
EP    2313523 A2    4/2011
(Continued)

OTHER PUBLICATIONS

A. McKenna et al. The Genome Analysis Toolkit: A MapReduce framework for analyzing next-generation DNA sequencing data. Genome Research. Published in advance Jul. 19, 2010. 20: 1297-1303.; http://genome.cshlp.org/ content/20/19/1297.full.html. Retrieved May 25, 2016.
(Continued)

*Primary Examiner* — Oleg Korsak
(74) *Attorney, Agent, or Firm* — Mintz Levin Cohn Ferris Glovsky and Popeo, P.C.

(57)    ABSTRACT

A method and system for correlating genome data with EMR/PHR data is disclosed herein. The method includes identifying a plurality of sources of genome data. The method also includes generating an index file for each of the plurality of genome files. The method also includes transmitting each index file to a central depository. The method also includes identifying electronic medical record (EMR) and/or personal health record (PHR) data at each source of the plurality of sources of genome data. The method also includes correlating each genome file of the plurality of genome files with a corresponding EMR/PHR data.

11 Claims, 7 Drawing Sheets

(51) Int. Cl.
*G06F 19/28* (2011.01)
*G06F 19/00* (2018.01)
*G06F 17/30* (2006.01)

(52) U.S. Cl.
CPC ............ *G06F 19/28* (2013.01); *G06F 19/322* (2013.01); *G06F 2212/1052* (2013.01)

(58) Field of Classification Search
USPC .......................................... 713/193; 705/2, 3
See application file for complete search history.

(56) References Cited

U.S. PATENT DOCUMENTS

| | | | |
|---|---|---|---|
| 6,112,288 | A | 8/2000 | Ullner |
| 6,253,529 | B1 | 7/2001 | De Boer |
| 6,681,186 | B1 | 1/2004 | Denisov et al. |
| 7,680,790 | B2 | 3/2010 | Indeck et al. |
| 7,917,299 | B2 | 3/2011 | Buhler et al. |
| 7,917,302 | B2 | 3/2011 | Rognes |
| 7,948,015 | B2 | 5/2011 | Rothberg et al. |
| 8,209,130 | B1 | 6/2012 | Kennedy et al. |
| 8,217,433 | B1 | 7/2012 | Fife |
| 8,280,640 | B2 | 10/2012 | Levin et al. |
| 8,445,945 | B2 | 5/2013 | Rothberg et al. |
| 8,524,487 | B2 | 9/2013 | Fife |
| 8,558,288 | B2 | 10/2013 | Rothberg et al. |
| 8,594,951 | B2 | 11/2013 | Homer |
| 8,620,923 | B1* | 12/2013 | Wormley .......... G06F 17/30106 707/741 |
| 8,936,763 | B2 | 1/2015 | Rothberg et al. |
| 9,014,989 | B2 | 4/2015 | McMillen et al. |
| 9,483,610 | B2 | 11/2016 | McMillen et al. |
| 9,576,103 | B2 | 2/2017 | McMillen et al. |
| 2003/0033279 | A1 | 2/2003 | Gibson et al. |
| 2003/0033501 | A1 | 2/2003 | Cooke et al. |
| 2003/0039362 | A1* | 2/2003 | Califano ............. G06F 21/6254 380/283 |
| 2003/0104470 | A1* | 6/2003 | Fors .................... G06Q 10/087 435/7.1 |
| 2004/0024536 | A1 | 2/2004 | Rognes |
| 2004/0059721 | A1 | 3/2004 | Patzer |
| 2004/0098203 | A1 | 5/2004 | Rognes |
| 2004/0126840 | A1 | 7/2004 | Cheng et al. |
| 2005/0060195 | A1* | 3/2005 | Bessette .................. G06F 19/28 705/2 |
| 2005/0131649 | A1 | 6/2005 | Larsen et al. |
| 2005/0228595 | A1 | 10/2005 | Cooke et al. |
| 2007/0038381 | A1 | 2/2007 | Melchior et al. |
| 2007/0078897 | A1* | 4/2007 | Hayashi ............ G06F 17/30038 |
| 2007/0088510 | A1 | 4/2007 | Li et al. |
| 2007/0196816 | A1 | 8/2007 | Schwartz et al. |
| 2008/0005024 | A1* | 1/2008 | Kirkwood ............ G06Q 10/00 705/50 |
| 2008/0086274 | A1 | 4/2008 | Chamberlain et al. |
| 2008/0250016 | A1 | 10/2008 | Farrar |
| 2009/0125248 | A1 | 5/2009 | Shams et al. |
| 2009/0171647 | A1 | 7/2009 | Mannava et al. |
| 2010/0077267 | A1 | 3/2010 | Perego et al. |
| 2010/0082805 | A1 | 4/2010 | Orton et al. |
| 2010/0169313 | A1* | 7/2010 | Kenedy ............ G06F 17/30867 707/736 |
| 2010/0281401 | A1 | 11/2010 | Tebbs et al. |
| 2011/0004413 | A1 | 1/2011 | Carnevali et al. |
| 2011/0093581 | A1* | 4/2011 | Venkatachalam ... H04L 63/0272 709/223 |
| 2011/0184235 | A1 | 7/2011 | Schostek et al. |
| 2012/0001615 | A1 | 1/2012 | Levine |
| 2012/0089339 | A1 | 4/2012 | Ganeshalingam et al. |
| 2012/0102041 | A1 | 4/2012 | Park et al. |
| 2012/0109849 | A1 | 5/2012 | Chamberlain et al. |
| 2012/0149981 | A1 | 6/2012 | Khait et al. |
| 2013/0110407 | A1 | 5/2013 | Baccash et al. |
| 2013/0124100 | A1 | 5/2013 | Drmanac et al. |
| 2013/0157870 | A1 | 6/2013 | Pushkarev et al. |
| 2013/0091121 | A1 | 8/2013 | Bhola et al. |
| 2013/0194882 | A1 | 8/2013 | Ishii et al. |
| 2013/0204851 | A1 | 8/2013 | Bhola et al. |
| 2013/0245958 | A1 | 9/2013 | Forster et al. |
| 2013/0296175 | A1 | 11/2013 | Rafnar et al. |
| 2013/0297221 | A1 | 11/2013 | Johnson et al. |
| 2013/0311106 | A1 | 11/2013 | White et al. |
| 2013/0316331 | A1 | 11/2013 | Isakov et al. |
| 2013/0324417 | A1 | 12/2013 | Kennedy et al. |
| 2013/0332081 | A1 | 12/2013 | Reese et al. |
| 2013/0338012 | A1 | 12/2013 | Sulem et al. |
| 2013/0338934 | A1 | 12/2013 | Asadi et al. |
| 2014/0024537 | A1 | 1/2014 | Rigatti et al. |
| 2014/0033125 | A1 | 1/2014 | Meral |
| 2014/0045705 | A1 | 2/2014 | Bustamante et al. |
| 2014/0046926 | A1* | 2/2014 | Walton .................. G06Q 50/22 707/710 |
| 2014/0051588 | A9 | 2/2014 | Drmanac et al. |
| 2014/0081665 | A1* | 3/2014 | Holmes ................ G06F 19/322 705/3 |
| 2014/0114582 | A1 | 4/2014 | Mittelman et al. |
| 2014/0121116 | A1 | 5/2014 | Richards et al. |
| 2014/0164516 | A1* | 6/2014 | Maltbie .................. H04L 67/06 709/204 |
| 2014/0200166 | A1 | 7/2014 | McMillen et al. |
| 2014/0236490 | A1 | 8/2014 | McMillen et al. |
| 2014/0304276 | A1 | 10/2014 | Boyce |
| 2014/0309944 | A1 | 10/2014 | McMillen et al. |
| 2014/0310215 | A1* | 10/2014 | Trakadis ................. G06F 19/28 706/13 |
| 2014/0316716 | A1 | 10/2014 | Jiang et al. |
| 2014/0337052 | A1* | 11/2014 | Pellini .................... G06Q 50/24 705/3 |
| 2014/0350968 | A1* | 11/2014 | Hahn ..................... G06F 19/322 705/3 |
| 2014/0368550 | A1 | 12/2014 | Vaske et al. |
| 2014/0371109 | A1 | 12/2014 | McMillen et al. |
| 2014/0371110 | A1 | 12/2014 | Van Rooyen et al. |
| 2015/0066824 | A1 | 3/2015 | Harris et al. |
| 2015/0123600 | A1 | 5/2015 | Groat et al. |
| 2015/0142334 | A1 | 5/2015 | Mishra |
| 2015/0154406 | A1 | 6/2015 | Naehrig et al. |
| 2015/0248525 | A1* | 9/2015 | Ury ........................ G06Q 50/24 705/3 |
| 2015/0286495 | A1 | 10/2015 | Lee |
| 2015/0310163 | A1 | 10/2015 | Kingsmore et al. |
| 2015/0339437 | A1 | 11/2015 | McMillen et al. |
| 2016/0046986 | A1 | 2/2016 | Eltoukhy et al. |
| 2016/0092631 | A1 | 3/2016 | Yandell et al. |
| 2016/0178569 | A1 | 6/2016 | Hoffman et al. |

FOREIGN PATENT DOCUMENTS

| | | |
|---|---|---|
| WO | 2011149534 | 12/2011 |
| WO | WO-2012/122546 A2 | 9/2012 |
| WO | 2013128371 | 9/2013 |
| WO | 2014060305 | 4/2014 |
| WO | 2014074246 | 5/2014 |
| WO | WO-2014/113736 A1 | 7/2014 |
| WO | WO-2014/121091 A1 | 8/2014 |
| WO | WO-2014/186604 A1 | 11/2014 |
| WO | WO-2015/051006 A2 | 4/2015 |
| WO | WO-2015/089333 A1 | 6/2015 |
| WO | WO-2015/100427 A1 | 7/2015 |
| WO | WO-2015/123600 A1 | 8/2015 |

OTHER PUBLICATIONS

Al Junid et al. "Development of Novel Data Compression Technique for Accelerate DNA Sequence Alignment Based on Smith-Waterman Algorithm." Highlighted. University Technology MARA (UiTM). 2009 Third UKSim European Symposium on Computer Modeling and Simulation. pp. 181-186.

Al Junid et al. "Optimization of DNA Sequences Data for Accelerate DNA Sequences Alignment on FPGA." University Technology Mara (UiTM). 2010 Fourth Asia International Conference on

(56) References Cited

OTHER PUBLICATIONS

Mathematical/Analytical Modelling and Computer Simulation. pp. 231-236.
Alachiotis, et al, Accelerating Phylogeny-Aware Short DNA Read Alignment with FPGAs, The Exelixis Lab, (2011) pp. 8, Heidelberg Institute for Theoretical Studies, Heidelberg, Germany.
Altera Corp, Implementation of the Smith-Waterman Algorithm on a Reconfigurable Supercomputing Platform, White Paper, 18 pgs Sep. 2007 Ver. 1.
Anonymous: "FPGA-accelerated Bioinformics at #ASHG-Dragen Aligner from Edico Genome." Oct. 20, 2014 (Oct. 20, 2014). XP055360856. Retrieved from the Internet: URL:http://moolog.us/blogs/glob/2014/210/20/fpga-accelerated-bioinformics-at-ashg-dragen-aligner-from-edico-genome/# [retrieved on Mar. 31, 2017]. 7 pages.
B. Langmead et al. Searching for SNPs with cloud computing. Genome Biology 2009, vol. 10: Iss, II: R134, Published: Nov. 20, 2009. 10 pages.
Benkrid et al, A highly parameterized and efficient FPGA-based skeleton for pairwise biological sequence alignment, IEEE Transactions on VLSI Systems, Apr. 2009, pp. 561-570 (1-12), IEEE Educational Activities Dept. Piscataway, NJ.
Buyukkurt et al, Compiler Generated Systolic Arrays for Wavefront Algorithm Acceleration on FPGAs, Sep. 2008, 4 pgs, International Conference on Field Programmable Logic and Applications, Heidelberg, Germany.
Chang, et al, Exploring Sequence Alignment Algorithms on FPGA-based Heterogeneous Architectures, Proceedings IWBBIO, pp. 330-341, 2014, Granada.
Choi, Young-kyu, et al. "A Quantitative Analysis of Microarchitectures of Modern CPU-FPGA Platforms." Design Automation Conference, Jun. 5-9, 2016, DAC '16, Jun. 5-9, 2016. Austin, TX. Conference Presentation. 6 pages.
Clive Maxfield. Impulse achieves 16X speed-up of genome analysis on $2,500 FPGA module. EE Times. Jun. 15, 2012. http://www.eetimes.com/ documentasp?doc id=1317288&print=yes. Retrieved Mar. 29, 2016. 4 pages.
Corey B. Olson et al. "Hardware Acceleration of Short Read Mapping." University of Washington, Pico Computing Inc., Fred Hutchinson Cancer Research CenterSeattle, WA. 2012. 8 pages.
Dydel, Stefan and Piotr Bala. "Large Scale Protein Sequence Alignment Using FPGA Reprogrammable Logic Devices.", Faculty of Mathematics and Computer Science. N. Copernicus University, 10 pgs, 2004, Torun, Poland.J. Becker, M. Platzner, S. Vernalde (Eds.): FPL 2004, LNCS 3203, pp. 23-32, 2004.
E. Fernandez, W. Najjar, E. Harris, and S. Lonardi. Exploration of Short Reads Genome Mapping in Hardwares. Field Programmable Logic and Applications (FPL), 20th Int. Conf. Milano, Italy, Aug. 2010. 4 pages.
Edward B. Fernandez et al. "Multithreaded FPGA Acceleration of DNA Sequence Mapping." University of California Riverside, Riverside and Jacquard Computing Inc, Riverside. 2012 IEEE. 6 pages.
Edward Fernandez et al. PowerPoint presentation on "Multithreaded FPGA Acceleration of DNA Sequence Mapping." UC Riverside, Department of Computer Science and Engineering Jacquard Computing. 2012. 20 pages.
Faes, et al, Scalable Hardware Accelerator for Comparing DNA and Protein Sequences, Infoscale, 2006, pp. 6, ACM, Hong Kong.
Fagin, FPGA and Rapid Prototyping Technology Use in a Special Purpose Computer for Molecular Genetics, Website: http://www.faginfamily.net/barry/Papers/ICCD92.htm, Thayer School of Engineering, Dartmouth, Hanover, NH. (1992). Retrieved Jan. 11, 2017. 6 pages.
G. Auwera et al. From FastQ data to high confidence variant calls: the Genome Analysis Toolkit best practices pipeline. HHS Public Access, Published online Oct, 15, 2013. http://www.ncbi.nlm.nih.gov/pmc/articles/PMC4243306/. Retrieved May 25, 2016. 27 pages.

Guccione et al, Gene Matching Using JBits, 9 pages Xilinx, Inc. San Jose CA (2002).
Guo, Xinyu et al. "A Systolic Array-Based FPGA Parallel Architecture for the BLAST Algorithm." ISRN Bioinformatics, 2012, 11 pages. vol. 2012. Article ID 195658.
Hall, Adam. "Short-Read DNA Sequence Alignment with Custom Designed FPGA-based Hardware." Master of Science Thesis. The University of Cambridge, 2007. 186 pages.
Harris et al, A Banded Smith-Waterman FPGA Accelerator for Mercury BLASTP, Research Report, (2007), pp. 5, BECS Technology, Inc./NIH/NGHRI, St. Louis, Missouri.
Hasan et al, An Overview of Hardware-Based Acceleration of Biological Sequence Alignment, Computational Biology and Applied Bioinformatics, Sep. 2011, pp. 187-202, InTech, Rijeka, Croatia.
Herbordt, Martin et al., "Single Pass Streaming BLAST on FPGAs", NIH Public Access Author Manuscript, Nov. 2007, 25 pgs, Parallel Comput.
Herbordt, Martin, et al., "Single Pass, BLAST-like, Approximate String Matching of FPGAs", Boston University, 2006, 19 pgs, Boston.
Hoang et al., FPGA Implementation of Systolic Sequence Alignment, 1991, 4 pgs. NSF Graduate Fellowship.
Hoang, A Systolic Array for the Sequence Alignment Problem, Apr. 1992, 25 pgs, Brown University, Providence, RI.
Hoang, Searching Genetic Databases on Splash 2, FCCM20 Endorsement, 1993, pp. 185-191, Brown University, Providence, RI.
Hughey, Parallel Hardware for Sequence Comparison and Alignment, Cabios, 1996, pp. 473-479, vol. 12 No. 6, Oxford University Press, CA.
International Search Report and Written Opinion issued in International Application No. PCT/US2017/013057, dated Apr. 11, 2017 (dated Nov. 4, 2017). 10 pages.
International Search Report and Written Opinion issued in International Application No. PCT/US2017/036424, dated Sep. 12, 2017 (dated Dec. 9, 2017). 12 pages.
International Search Report dated Jun. 18, 2014, for PCT application No. PCT/US2014/012144. 2 pages.
Isaac TS Li et al. Methodology article, 160-fold acceleration of the Smith-Waterman algorithm using a field programmable gate array (FPGA).: Published Jun. 7, 2007. BMC Bioinformatics 2007, 8:185, Institute of Biomaterials and Biomedical Engineering, University of Toronto,Ontario, Canada. 7 pages.
Jacob, Arpith et al. "FPGA-Accelerated seed generation in Mercury BLASTP", Washington University in St. Louis, BECS Technology Inc. (2007). 10 pgs.
Kasap, Server et al, "Design and Implementation of an FPGA-based Core for Gapped BLAST Sequence Alignment with the Two-Hit Method", Engineering Letters, 16:3 EL_16_3_25, Aug. 20, 2012, 10 pgs, Scotland, UK (2008).
Khaled Benkrid et al. Review Article: "High Performance Biological Pairwise Sequence Alignment: FPGA versus GPU versus Cell BE versus GPP." Hindawi Publishing Corporation. International Journal of Reconfigurable Computing. vol. 2012. (2012). 15 pages. Institute of Integrated Systems, School of Engineering, The University of Edinburgh, Kings Edinburgh, UK and Electrical and Computer Engineering Department, The University of Arizona, Tucson, AZ.
Lancaster Joseph, "Design and Evaluation of a BLAST Ungapped Extension Accelerator, Master's Thesis", Washington University, Jan. 1, 2006, 79 pgs, Report No. WUCSE-20016-21, 2006 St. Louis.
Lancaster Joseph, et al. "Acceleration of Ungapped Extension in Mercury BLAST", MSP—7th Workshop on Media and Streaming Processors, Nov. 2005, 9 pgs.
Lavenier, Dominique. "SAMBA: Systolic Accelerator for Molecular Biological Applications." Research Report RR-2845, INRIA. 22 pgs, Mar. 1996, France.
Lemoine, et al, High Speed Pattern Matching in Genetic Data Base with Reconfigurable Hardware, ISMB-94 Proceedings, 1994, pp. 269-275, AAAI (www.aaai.org), France.

(56) References Cited

OTHER PUBLICATIONS

Lopresti, Rapid Implementation of a Genetic Sequence Comparator Using Field-Programmable Logic Arrays, Advanced Research in VLSI, 1991, pp. 138-152, UC Santa Cruz, CA.
M. Ruffalo, T. LaFramboise, and M. Koyuturk. Comparative analysis of algorithms for next-generation sequencing read alignment. Bioinformatics (2011) 27 (20): 2790-2796. First published online: Aug. 19, 2011. https://bioinformatics.oxfordjournals.org/content/27/20/2790.full, Retrieved May 25, 2016.
M. Schatz, B. Langmead, and S. Salzberg. Cloud Computing and the DNA Data Race. HHS Public Access. Published Nat Biotechnol. Jul. 2010; 28(7): 691-693. http://www.ncbi.nlm.nih.gov/pmciarticles/PMC2904649/. Retrieved May 25, 2016.
M. Schatz, C. Trapnell, A. Delcher, and A. Varshney. High-throughput sequence alignment using Graphics Processing Units. Published Dec. 10, 2007. BMC Bioinformatics. http://bmcbioinformatics.biomedcentral.com/; articles/10.1186/1471-2105-8-474. Retrieved May 25, 2016. 13 pages.
Mahram, FPGA Acceleration of Sequence Analysis Tools in Bioinformatics, Dissertation, 2013, 180 pages, Boston, MA.
Michael Schatz. CloudBurst: highly sensitive read mapping with MapReduce. Bioinformatics (2009) 25 (11): 1363-1369. First published online: Apr. 8, 2009. http://bioinformatics.oxfordjournals.org/content/25/11/1363.full. Retrieved May 25, 2016.
Mikami, et al, Efficient FPGA-based Hardware Algorithms for Approximate String Matching, ITC-CSCC, 2008, pp. 201-204, Hiroshima, JP.
Miller, Neil A. et al. "A 26-hour system of highly sensitive whole genome sequencing for emergency management of genetic diseases." Genome Medicine. vol. 7, No. 100, Sep. 30, 2015 (Sep. 30, 2015). 16 pages.
Moritz, et al, Implementation of a Parallel Algorithm for Protein Pairwise Alignment Using Reconfigurable Computing, Conference date 2006, Published Feb. 12, 2007. pp. 7, Brazilian National Research Counsel (CNPq), Brazil.
Muriki, Krishna et al., "RC-BLAST: Towards a Portable, Cost-Effective Open Source Hardware Implementation" Supported in part by NSF Grant EIA-9985986, (2005). 8 pgs.
N. Homer, B. Merriman, and S. Nelson. BFAST: An Alignment Tool for Large Scale Genome Resequencing. PLOS. Published Nov. 11, 2009. 11 pages. http://journals.plos.org/plosone/article?id=10.1371/journal.pone.0007767. Retrieved May 25, 2016.
Nawaz, et al, A Parallel FPGA Design of the Smith-Waterman Traceback, Conference date 2010. Published Jan. 6, 2011, pp. 6, ACE Associated Compiler Expert, The Netherlands.
Nawaz, et al, Fast Smith-Waterman hardware implementation, hArtes (IST-035143), (2010) pp. 4, The Morpheus (IST-027342) and RCOSY (DES-6392) Projects.
Nelson, et al, Shepard: A Fast Exact Match Short Read Aligner, Research Report, (2012) pp. 4, Dept. of Electrical and Computer Engineering, Iowa State University, Ames, IA.
Oliver, et al, Using Reconfigurable Hardware to Accelerate Multiple Sequence Alignment with ClustalW, Bioinformatics, 2005, pp. 3431-3432, vol. 21 No. 16, Advanced Access Publication, Singapore.
Oliver, Hyper Customized Processors for Bio-Sequence Database Scanning on FPGAs, FPGA, pp. 229-237, 2005 Monterey, CA.
Olson, Corey Bruce. "An FPGA Acceleration of Short Read Human Genome Mapping." Master of Science Thesis. University of Washington, 2011. 103 pages.
S. Angiuoli and S. Salzberg, Mugsy: fast multiple alignment of closely related whole genomes, Bioinformatics (2011) 27 (3): 334-342. First published online: Dec. 9, 2010. http://bioinformatics.oxfordjournals.org/content/27/31334.full. Retrieved May 25, 2016.
Sakar, Souradip et al. "Network-on-Chip Hardware Accelerators for Biological Sequence Alignment." IEEE Transactions on Computers, Jan. 2010, vol. 59, No, 1, pp. 29-41, Washington State.
Sotiriades Euripides, et al. "FPGA based Architecture for DNA Sequence Comparison and Database Search", University of Crete, 2006, 8 pgs, Crete, Greece.
Sotiriades Euripides, et al., "Some Initial Results on Hardware BLAST acceleration with a Reconfigurable Architecture", University of Crete, 2006, 8 pgs, Crete, Greece.
T. Derrien et al. Fast Computation and Applications of Genome Mappability. PLOS One. Published: Jan. 19, 2012. 15 pages. http://journals.plos.org/plosone/article?id=10.1371/journal.pone.0030377. Retrieved May 25, 2016.
T. Hardcastle and K. Kelly. baySeq: Empirical Bayesian methods for identifying differential expression in sequence count data. Published Aug. 10, 2010, BMC Bioinformatics. http://bmcbioinformatics.biomedcentral.com/ articles/10,1186/1471-2105-11-422. Retrieved May 25, 2016. 16 pages.
Thomas D. Wu and Colin K. Watanabe. Sequence analysis: "GMAP: a genomic mapping and alignment program for mRNA and EST sequences." Publication Feb. 22, 2005. Bioinformatics Original Paper. vol. 21 No. 9 2005, pp. 1859-1875. South San Francisco, CA.
Tim Oliver et al. "Multiple Sequence Alignment on an FPGA." IEEE Computer Society. School of Computer Engineering, Nanyang Technological University, Singapore; Project Proteus, School of Engineering, Ngee Ann Polytechnic, Singapore. Proceedings of the 2005 11th International Conference on Parallel and Distributed Systems. (2005). 5 pages.
TimeLogic Division, Active Motif Inc., "Accelerated BLAST Performance with Tera-Blast: a comparison of FPGA versus GPU and CPU Blast implementations", Technical Note, May 2013, 5 pages, Version 1.0.
Van Court et al., Families of FPGA-Based Algorithms for Approximate String Matching, (2004), 11 pgs, Boston University, ECE Dept., MA.
W. Zhang et al. A Practical Comparison of De Novo Genome Assembly Software Tools for Next-Generation Sequencing Technologies. PLOS One. Published: Mar. 14, 2011. http://journals.plos.org/plosone/article?id=10.1371/ journal.pone.0017915. Retrieved May 25, 2016. 10 pages.
Yamaguchi, et al,, High Speed Homology Search with FPGAs, Pacific Symposium on Biocomputing 7:271-282 (2002), Japan.
Ying Liu et al. "An FPGA-Based Web Server for High Performance Biological Sequence Alignment." The University of Edinburgh, Edinburgh, UK and The Queen's University of Belfast, Northern Ireland, UK. 2009 NASA/ESA Conference on Adaptive Hardware and Systems. pp. 361-368.
Yu, et al, A Smith-Waterman Systolic Cell, (2003), 10 pgs. Dept. of Computer Science, The Chinese University of Hong Kong.

\* cited by examiner

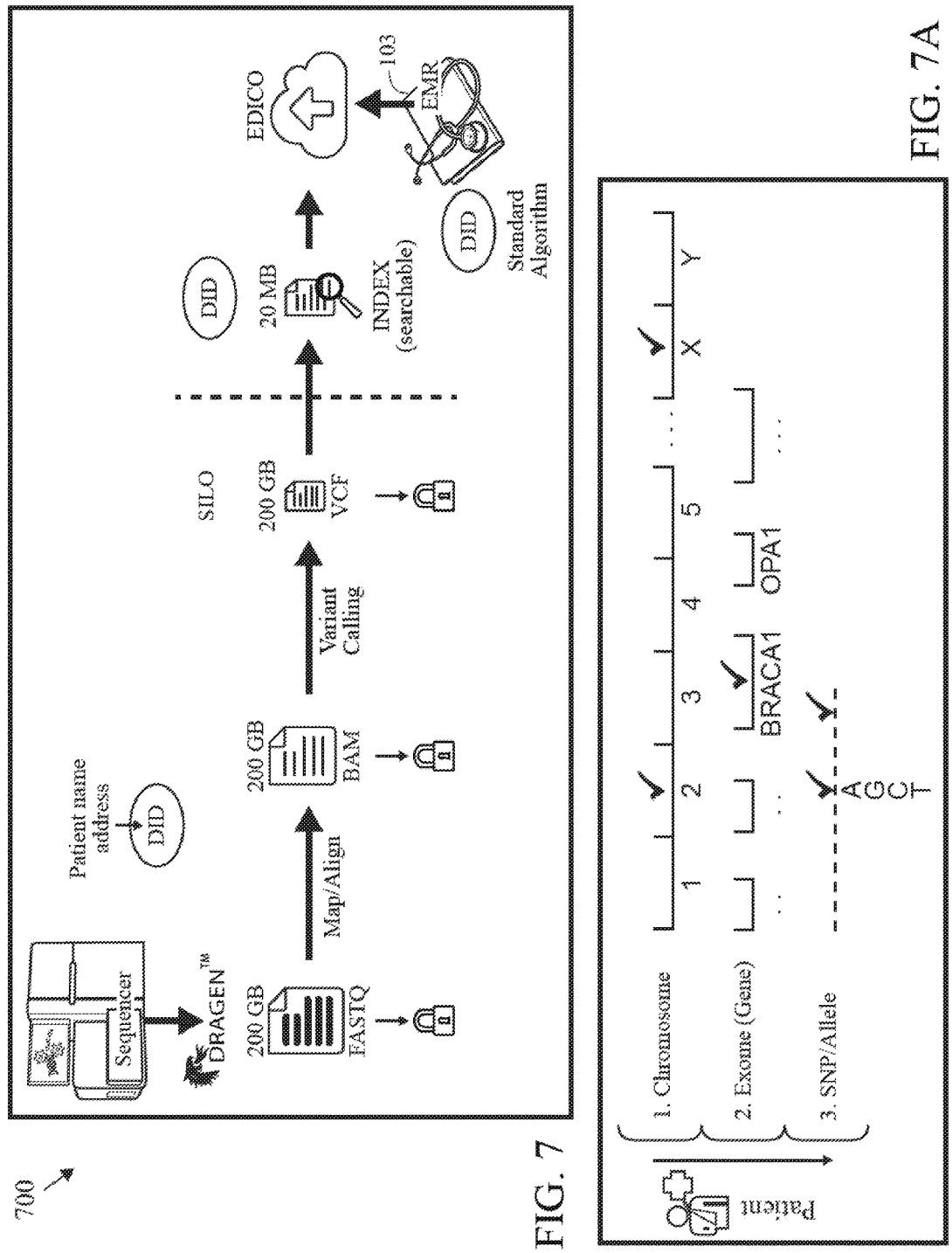

METHOD AND SYSTEM FOR GENOMIC VISUALIZATION

CROSS REFERENCE TO RELATED APPLICATION

The present application claims priority to U.S. Provisional Patent Application No. 62/137,103, filed on Mar. 23, 2015, which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to genomic visualization.

Description of the Related Art

Genomic visualization tools have been devised to assist researchers, laboratories, and other users to visually display and understand genomic data. The genomic data is often in the form of individual samples having chromosomal data (including measurements of at least one event at a particular location on the chromosomes). An event here would indicate some measurement related to the genome. Examples of such measurements include the expression of a gene, an exon at a particular location, the number of copies of a portion of the genome that have been gained or lost, the extent of methylation of the genome at a particular location, the affinity of certain promoters to bind to a particular area on the genome, etc. In some cases, users may calculate a frequency of event based on a frequency of occurrence of the event in the selected sample. For example, it may be desirable to calculate the frequency of aberration, such as the frequency of a gain or loss of chromosomal copies when compared to a reference sample in a selected population of samples. In other circumstances, it may be desirable to review an annotation regarding specific information as related to a particular chromosomal region of the chromosome. Such information might include items such as what genes are present in a location and if there are known copy number polymorphisms in that area (including a list of such polymorphisms). Other items might include information pertaining to the presence of miroRNAs and potential Single Nucleotide Polymorphism (SNP)s in the area, etc.

Genomic data are available from public or private databases and academic or commercial diagnostic laboratories. Genomic data can also be obtained by sequencing the entire genome of an individual, or a portion thereof. Suitable methods of DNA sequencing include Sanger sequencing, polony sequencing, pyrosequencing, ion semiconductor sequencing, single molecule sequencing, and the like. Sequenced genomic data can be provided as electronic text files, html files, xml files and various other regular databases formats.

Existing systems available for visualization of chromosomal or genomic annotations, such as the University of California of Santa Cruz browser and the Ensemble Genome Browser, display various annotations for a specific region of the genome. Ensemble is a joint project between the European Molecular Biology Laboratory, the European Bioinformatics Institute and the Wellcome Trust Sanger Institute.

The molecular data to be processed in a bioinformatics based platform typically concerns genomic data, such as Deoxyribonucleic acid (DNA) data. For example, a well-known method for generating DNA data involves DNA sequencing. DNA sequencing can be performed manually, such as in a lab, or may be performed by an automated sequencer, such as at a core sequencing facility, for the purpose of determining the genetic makeup of a sample of an individual's DNA. The person's genetic information may then be used in comparison to a referent, e.g., a reference genome, so as to determine its variance therefrom. Such variant information may then be subjected to further processing and used to determine or predict the occurrence of a diseased state in the individual.

Manual or automated DNA sequencing may be employed to determine the sequence of nucleotide bases in a sample of DNA, such as a sample obtained from a subject. Using various different bioinformatics techniques these sequences may then be assembled together to generate the genomic sequence of the subject, and/or mapped and aligned to genomic positions relative to a reference genome. This sequence may then be compared to a reference genomic sequence to determine how the genomic sequence of the subject varies from that of the reference. Such a process involves determining the variants in the sampled sequence and presents a central challenge to bioinformatics methodologies. Genomic data includes sequences of the DNA bases adenine (A), guanine (G), cytosine (C) and thymine (T). Genomic data includes sequences of the RNA bases adenine (A), guanine (G), cytosine (C) and uracil (U). Genomic data also includes epigenetic information such as DNA methylation patterns, histone deacetylation patterns, and the like.

"Phenotypic traits" are an organism's observable characteristics, including but not limited to its morphology, development, biochemical or physiological properties, behavior, and products of behavior (such as a bird's nest). Phenotypic traits also include diseases, such as various cancers, heart disease, Age-related Macular Degeneration, and the like.

Non-limiting general definitions for terms utilized in the pertinent art are set forth below.

Allele is any two or more alternative forms of the same gene that have the same relative position on homologous chromosomes.

BAM format is a binary alignment map format, which is the binary version of SAM.

Chromosome is a strand of DNA that is encoded with genes.

DNA is deoxyribonucleic acid, which contains the genetic code. It consists of two nucleotide chains in a double helix and joined by hydrogen bonds between complimentary bases of adenine and thymine, and cystosine and guanine.

Exome is part of the genome formed by exons, the sequences which when transcribed remain within the mature RNA after the introns are removed by RNA splicing.

Genome is the full set of chromosomes, the genetic material of an organism, and includes genes and non-coding sequences of DNA/RNA.

Hypertext Transfer Protocol ("HTTP") is a set of conventions for controlling the transfer of information via the Internet from a web server computer to a client computer, and also from a client computer to a web server, and Hypertext Transfer Protocol Secure ("HTTPS") is a communications protocol for secure communication via a network from a web server computer to a client computer, and also from a client computer to a web server by at a minimum verifying the authenticity of a web site.

Internet is the worldwide, decentralized totality of server computers and data-transmission paths which can supply information to a connected and browser-equipped client computer, and can receive and forward information entered from the client computer.

Nucleic acid library is a plurality of polynucleotide molecules that are prepared, assemble and/or modified for a specific process.

Phenotype is the composite of an organism's observable characteristics or traits, such as its morphology, development, biochemical or physiological properties, phenology, behavior, and products of behavior. A phenotype results from the expression of an organism's genes as well as the influence of environmental factors.

SAM is sequence alignment map format is a text format of mapping sequence reads (sequence information from a fragment whose physical genomic position is unknown) with a matching sequence in a reference genome.

Single Nucleotide Polymorphism ("SNP") is a DNA sequence variation occurring when a single nucleotide in the genome differs between members of a species (or between paired chromosomes in an individual).

URL or Uniform Resource Locator is an address on the World Wide Web.

User Interface or UI is the junction between a user and a computer program. An interface is a set of commands or menus through which a user communicates with a program. A command driven interface is one in which the user enter commands. A menu-driven interface is one in which the user selects command choices from various menus displayed on the screen.

Variant calling is a method of identifying factual differences between sequence reads of test samples and a reference sequence. Variant calling is used to identify somatic variants with a high degree of confidence.

Web-Browser is a complex software program, resident in a client computer, that is capable of loading and displaying text and images and exhibiting behaviors as encoded in HTML (HyperText Markup Language) from the Internet, and also from the client computer's memory. Major browsers include MICROSOFT INTERNET EXPLORER, NETSCAPE, APPLE SAFARI, MOZILLA FIREFOX, and OPERA.

Web-Server is a computer able to simultaneously manage many Internet information-exchange processes at the same time. Normally, server computers are more powerful than client computers, and are administratively and/or geographically centralized. An interactive-form information-collection process generally is controlled from a server computer, to which the sponsor of the process has access.

There is a need for distributing genomic data from a source to a recipient in a secure and efficient means.

BRIEF SUMMARY OF THE INVENTION

One aspect of the present invention is a method for correlating genome data with EMR/PHR data. The method includes identifying a plurality of sources of genome data. Each source of the plurality of sources comprises a plurality of genome files. The method also includes indexing and encrypting each of the plurality of genome files utilizing a processor at a source site for the source. Each of the plurality of genome files is identified with a unique DID. The method also includes generating an index file for each of the plurality of genome files. The method also includes transmitting each index file to a central depository. Each index file is stored as part of a plurality of index files. The method also includes identifying electronic medical record (EMR) and/or personal health record (PHR) data at each source of the plurality of sources of genome data. Each EMR/PHR data has a unique DID, and each EMR/PHR data matches a genome file of the plurality of genome files. The method also includes correlating each genome file of the plurality of genome files with a corresponding EMR/PHR data.

Another aspect of the present invention is a system for searching correlated genome data and EMR data. The system comprises a central depository site, a plurality of sources for genome data, a plurality of sources for EMR/PHR data, and search browser. The central depository site comprises a plurality of index files. Each of the plurality of index files represents encrypted genome files. Each of plurality of sources for genome data comprises a database of encrypted genome files. Each of the plurality of encrypted genome files has a unique DID. Each of the plurality of sources for EMR/PHR data comprises a database of EMR/PHR files. Each of the plurality of EMR/PHR files has a unique DID. Each EMR/PHR file matches a genome file having the same unique DID. The browser is for searching the plurality of index files.

Yet another aspect of the present invention is a method for privacy controlled genomic visualization. The method includes indexing and encrypting each of the plurality of genome files utilizing a processor at a source site. Each of the plurality of genome files is identified with a unique DID. The method also includes generating an index file for each of the plurality of genome files. The method also includes transmitting each index file to a brokering server. Each index file is stored as part of a plurality of searchable index files. The method also includes identifying electronic medical record (EMR) and/or personal health record (PHR) data at each source of a plurality of sources of genome data. Each EMR/PHR data has a unique DID. Each EMR/PHR data matches a genome file of the plurality of genome files. The method also includes matching each genome file of the plurality of genome files with a corresponding EMR/PHR data. The method also includes searching the plurality of searchable index files at a browser for the brokering server. The owner of an encrypted genome file controls access to the encrypted genome file and tracks the encrypted genome file.

Yet another aspect of the present invention is a method for privacy controlled genomic visualization. The method includes searching a plurality of index files for a specific genome level. Each of the plurality of index files represents encrypted genome data for an owner of the data. The specific level is selected from a chromosome level, an exome level, a gene level, an allele panel, or at an individual SNP or allele level. The method also includes identifying a set of index files of the plurality of index files for review. The method also includes requesting permission for access to the encrypted genome data and EMR/PHR data from an owner of the data for each index file of the set of index files. The method also includes receiving permission from the owner of the data. The method also includes receiving the genome data and the EMR/PHR data.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 7 is a block diagram for a method for processing of the genomic data at the genomic data site.

FIG. 7A is an illustration of an index file for a patient.

DETAILED DESCRIPTION OF THE INVENTION

Figure 1:
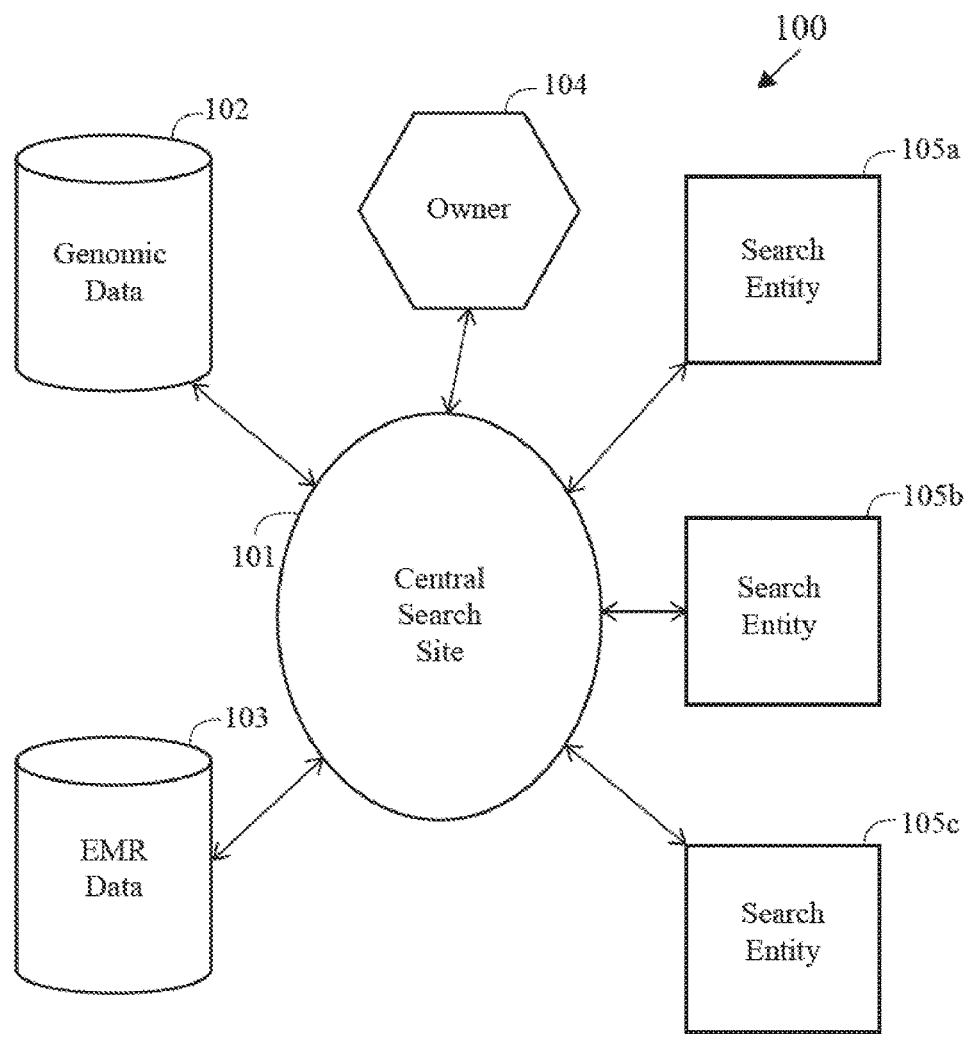
FIG. 1 is a block diagram of a system for genomic visualization with privacy control.

A system 100 for genomic visualization with privacy control is shown in FIG. 1. The system 100 includes a central depository site 101, a source of genomic data 102, a source of EMR data 103, and owner 104 (the patient) of the genomic data and EMR data, and a plurality of search entities 105a-c. The central depository site 101 functions as a brokerage of data between sources that have generated genomic data 102 and EMR data 103, and multiple searchers that utilize the information for academic, commercial and other purposes. The search entities 105 are researchers like universities, biotechnology companies, hospitals, and the like. The owner 104 preferably controls access to the unencrypted data and also tracks the data as it is distributed to search entities 105a-c.

The EMR data of a patient includes general health records, medical procedure records, allergies, illnesses, and the like of the patient.

The genomic data is preferably encrypted and indexed and stored locally. Thus, the central site 101 is not a warehouse of data, requiring an enormous storage data facility. The central site 101 only maintains a plurality of index files that can be easily searched. Further, the processing of the genomic data is performed at the genomic data site 102. A general process for processing the genomic data involves processing sequence data to generate a sequenced data file, processing the sequenced data file to generate an aligned data file, and processing the aligned data file to generate a variant called data file (VCF). One specific process for processing the genomic data involves processing sequence data to generate a FASTQ file, processing the FASTQ file to generate a binary sequence alignment map (BAM) file, and processing the BAM file to generate a variant call file (VCF). A more detail description is set forth in Van Rooyen et al., U.S. Patent Publication Number 20140371110 for Bioinformatics Systems, Apparatuses, and Methods Executed On An Integrated Circuit Processing Platform, which is hereby incorporated by reference in its entirety. The VCF is indexed into an index file and then encrypted. A DID (De-identified Identifier, e.g., a unique ID token that includes no identifying information like a patient's email, phone number, date-of-birth, zip, etc.) number is provided to each index file to maintain privacy and anonymity. The algorithm utilized to generate the DID for the index file is the same one used for the EMR data, and therefore the files can be matched based on the DID number.

The index files are transmitted from each genomic data site 102 to the central site 101. The index files are searchable at a chromosome level, exome level, gene level, allele panel, or at an individual SNP or allele level.

Figure 2:
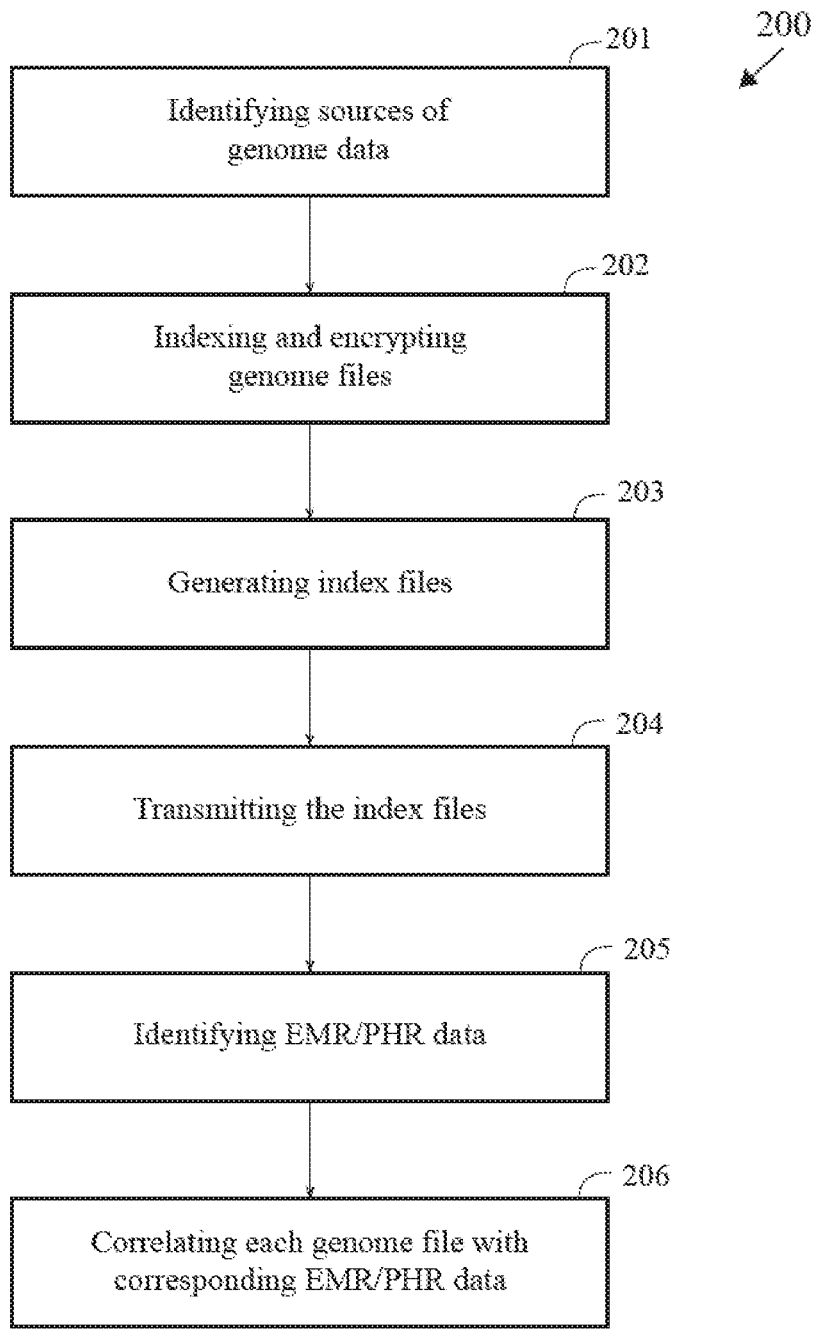
FIG. 2 is a flow chart for a method for correlating genome data with EMR/PHR data.

FIG. 2 illustrates a flow chart for a method 200 for correlating genome data with EMR/PHR data. At block 201, sources of genome data are identified. Each source comprises a plurality of genome files. At block 202, each of the plurality of genome files indexed and encrypted utilizing a processor at a source site for the source. Each of the plurality of genome files is identified with a unique DID. At block 203, an index file is generated for each of the plurality of genome files. At block 204, each index file is transmitted to a central depository site. Each index file is stored as part of a plurality of index files. At block 205, the electronic medical record (EMR) and/or personal health record (PHR) data is identified at each source of the plurality of sources of genome data. Each EMR/PHR data has a unique DID, and each EMR/PHR data matches a genome file of the plurality of genome files. At block 206, each genome file of the plurality of genome files is correlated with a corresponding EMR/PHR data.

Figure 3:
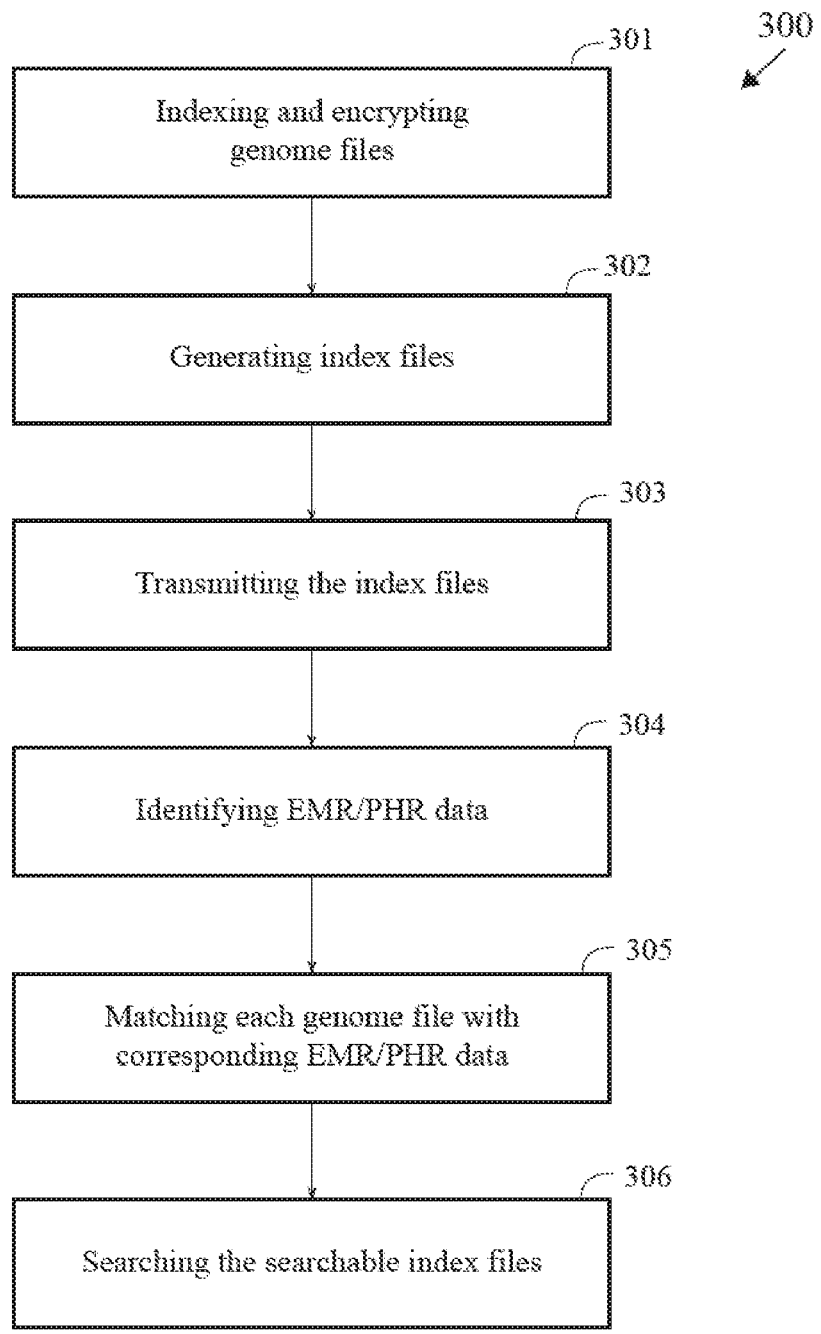
FIG. 3 is a flow chart for a method for privacy controlled genomic visualization.

FIG. 3 illustrates a flow chart for a method 300 for privacy controlled genomic visualization. At block 301, each of the plurality of genome files is indexed and encrypted utilizing a processor at a source site. Each of the plurality of genome files is identified with a unique DID. At block 302, an index file is generated for each of the plurality of genome files. At block 303, each index file is transmitted to a brokering server. Each index file is stored as part of a plurality of searchable index files. At block 304, electronic medical record (EMR) and/or personal health record (PHR) data is identified at each source of a plurality of sources of genome data. Each EMR/PHR data has a unique DID. Each EMR/PHR data matches a genome file of the plurality of genome files. At block 305, each genome file of the plurality of genome files is matched with a corresponding EMR/PHR data. At block 306, the plurality of searchable index files is search at a browser for the brokering server. The owner of an encrypted genome file controls access to the encrypted genome file and tracks the encrypted genome file.

Figure 4:
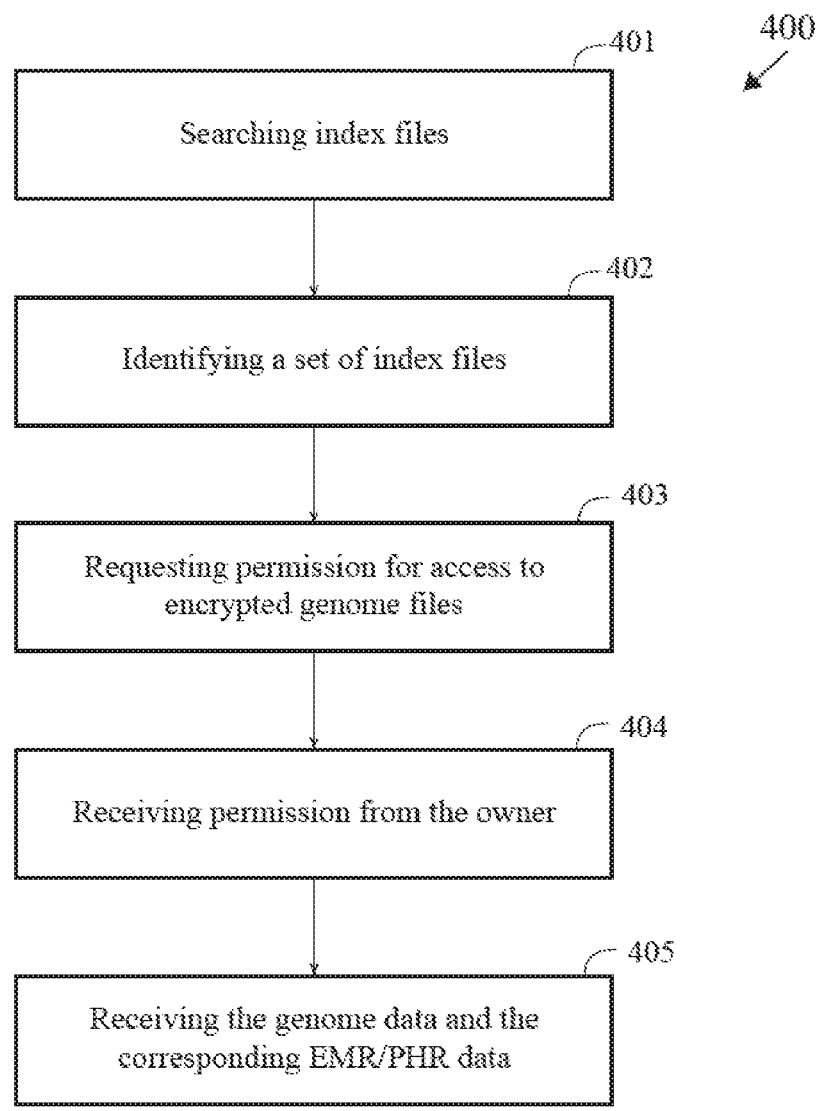
FIG. 4 is a flow chart for a method for privacy controlled genomic visualization.

FIG. 4 illustrates a flow chart for a method 400 for privacy controlled genomic visualization. At block 401, a plurality of index files is searched for a specific genome level. Each of the plurality of index files represents encrypted genome data for an owner of the data. The specific level is selected from a chromosome level, an exome level, a gene level, an allele panel, or at an individual SNP or allele level. At block 402, a set of index files of the plurality of index files is identified for review. At block 403, permission for access to the encrypted genome data and EMR/PHR data is requested from an owner of the data for each index file of the set of index files. At block 404, permission is received from the owner of the data. At block 405, the genome data and the EMR/PHR data are received by the searcher.

Figure 5:
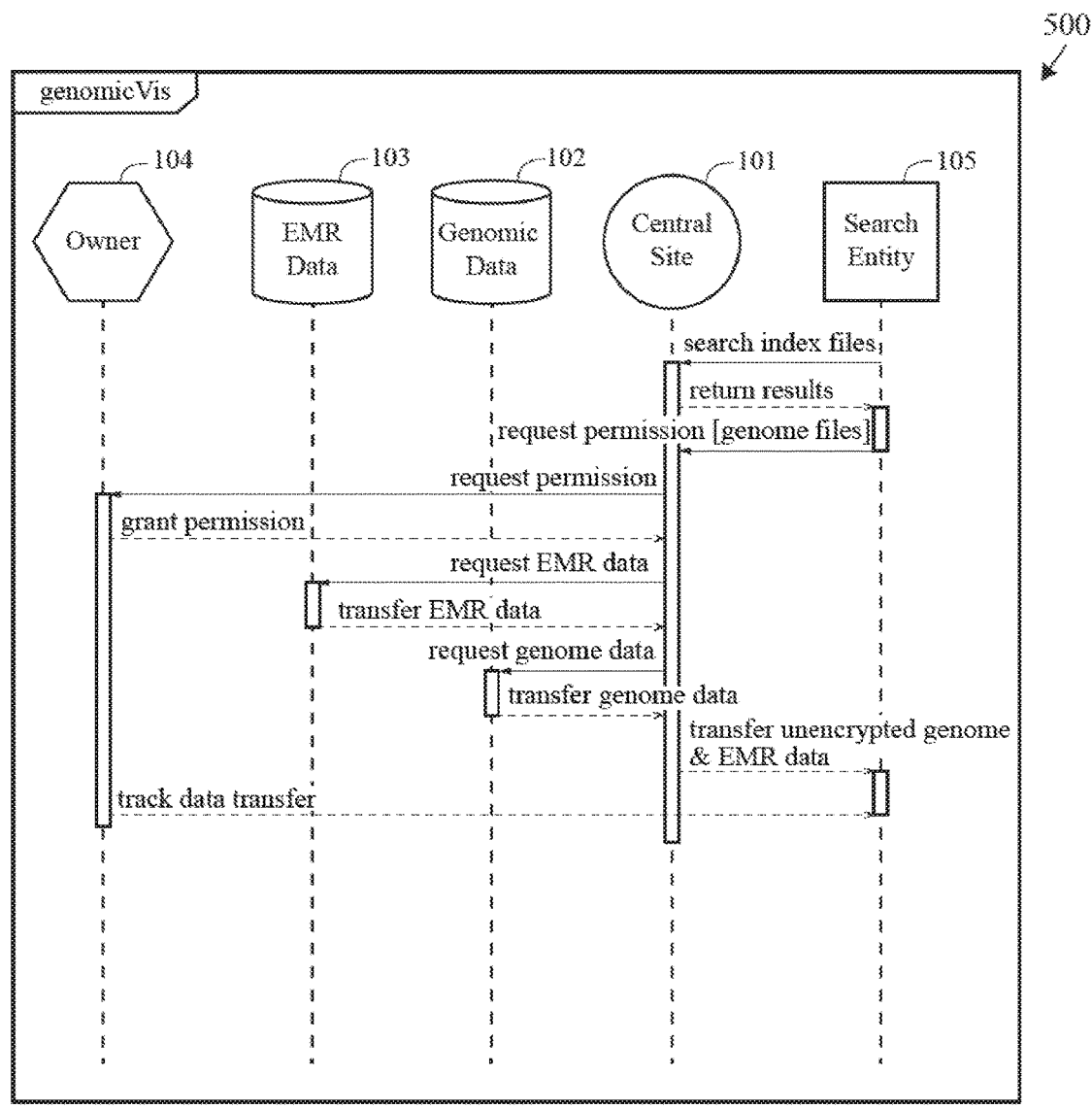
FIG. 5 is a communications sequence diagram for genomic visualization.

FIG. 5 illustrates a communication sequence diagram 500 for genomic visualization with privacy control. A search entity 105 searches the index files available at the central search site 101 using a central site browser. The search results are returned to the search entity 105. The search entity then requests permission for the unencrypted genome files which are represented by some or all of the index files. Since the index files only provide information on a variation, with no identifying information, the search entity must now receive permission from the owner of the genome to gain access to the more detailed information. The central search site 101 acts as a broker and presents the request to the owner. Preferably, the requests involve details behind the research so that the owner will know what his or her information is to be used for by the search entity 105. The owner then grants permission to the central search site 105 for access to the unencrypted genome data and the EMR data that matches the genome data. The central search site 101 then requests that the EMR data file be sent from the EMR data site 103, and that the genome data be sent from the genomic data site 102. The central search site 101 unencrypts the data and transfers the EMR data and the genome data to the search entity 105. The owner 104 tracks the data sent to the search entity, enabling privacy control by the owner 104.

Figure 6:
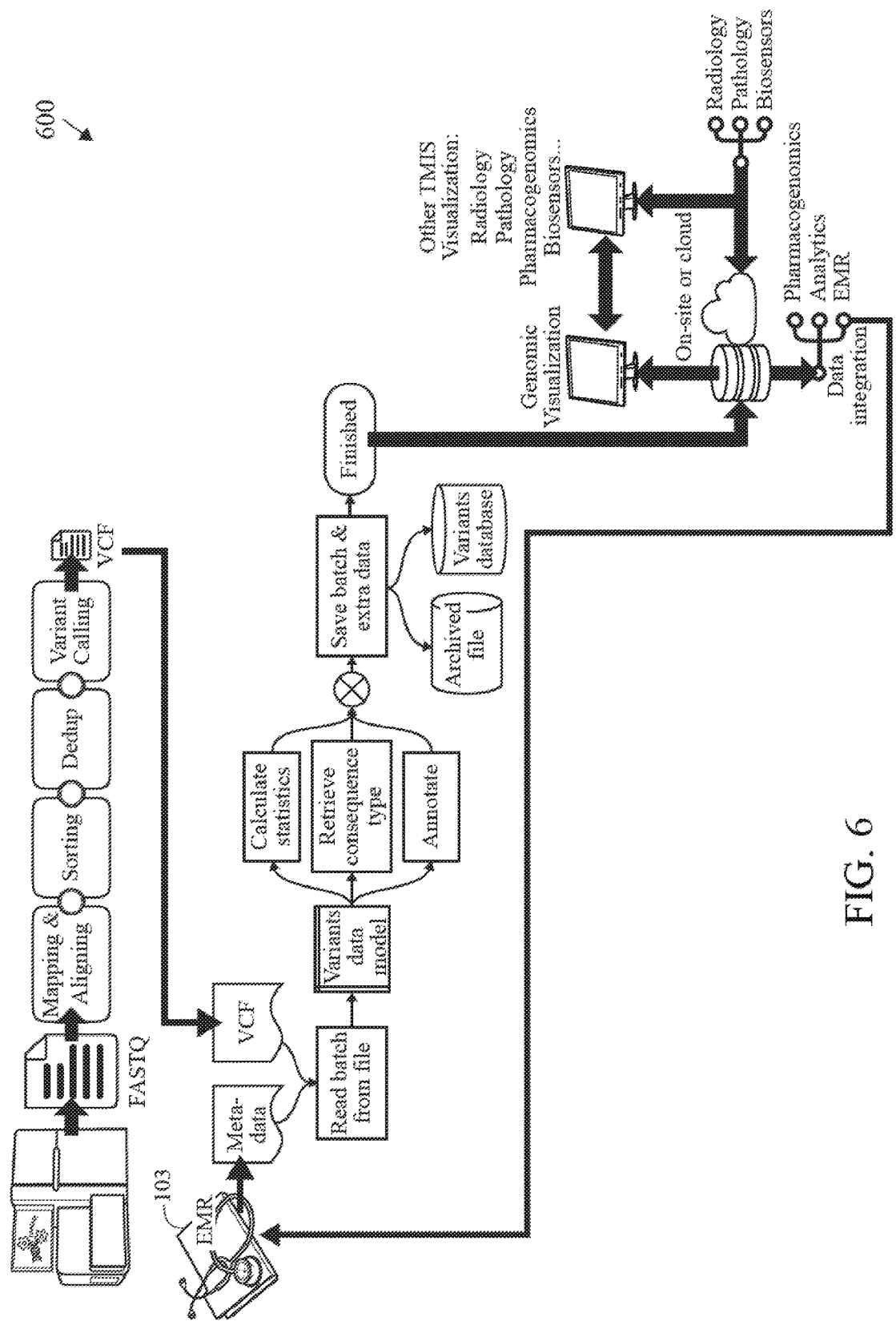
FIG. 6 is a block diagram for a method for genomic visualization.

FIG. 6 is a block diagram for a method 600 for genomic visualization.

FIG. 7 is a block diagram for a method 700 for processing of the genomic data at the genomic data site. FIG. 7A is an illustration of an index file for a patient.

The networks utilized with the present invention may be one or more of a wireless network, a wired network or any combination of wireless network and wired network. The networks utilized may include one or more of an Internet network, a wireless local area network ("LAN"), a cellular network, a fiber optics network, a passive optical network, a cable network, a satellite network (e.g., operating in Band C, Band Ku or Band Ka), a Global System for Mobile Communication, a Personal Communication Service, a Personal Area Network Wi-Fi, Fixed Wireless Data, IEEE 802.11a, 802.11b, 802.15.1, 802.11n and 802.11g or any other wired or wireless network for transmitting and receiving a data signal. The network may utilize one or more protocols of one or more network elements to which it is communicatively coupled. The network may translate to or from other protocols to one or more protocols of devices connected to the network. The invention may utilized a plurality of interconnected networks, such as, for example, a service provider network, the Internet, a broadcaster's network, a cable television network, a corporate network, and a home net.

Each of the interface descriptions preferably discloses use of at least one communication protocol to establish handshaking or bi-directional communications. These protocols preferably include but are not limited to XML, HTTP, TCP/IP, Serial, UDP, FTP, Web Services, WAP, SMTP, SMPP, DTS, Stored Procedures, Import/Export, Global Positioning Triangulation, IM, SMS, MMS, GPRS and Flash. The storage of data may be network accessible storage and may be local, remote, or a combination thereof. The storage of data may utilize a redundant array of inexpensive disks, tape, disk, a storage area network, an interne small computer systems interface a common Internet File System, network attached storage, a network file system, or other computer accessible storage. The databases used with the system preferably include but are not limited to MSSQL, Access, MySQL, Progress, Oracle, DB2, Open Source DBs and others. Operating system used with the system preferably include Microsoft 2010, XP, Vista, 200o Server, 2003 Server, 2008 Server, Windows Mobile, Linux, Android, Unix, I series, AS 400 and Apple OS.

The underlying protocol at a server is preferably Internet Protocol Suite (Transfer Control Protocol/Internet Protocol ("TCP/IP")), and the transmission protocol to receive a file is preferably a file transfer protocol ("FTP"), Hypertext Transfer Protocol ("HTTP"), Secure Hypertext Transfer Protocol ("HTTPS") or other similar protocols. The transmission protocol ranges from SIP to MGCP to FTP and beyond. The protocol at the server is preferably HTTPS.

It is further noted that the software described herein may be tangibly embodied in one or more physical media, such as, but not limited to, a compact disc ("CD"), a digital versatile disc ("DVD"), a floppy disk, a hard drive, read only memory ("ROM"), random access memory ("RAM"), as well as other physical media capable of storing software, or combinations thereof.

Numerous references were made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions. The genomic visualization system may utilize various computing devices including servers, graphical user interfaces, databases, engines, controllers, or other types of computing devices operating individually or collectively. One skilled in the pertinent art will appreciate that the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the invention. In preferred embodiments, the servers, databases, or interfaces preferably exchange data using standardized protocols or algorithms, possibly based on HTTP, HTTPS, AES, public-private key exchanges, web service APIs, known financial transaction protocols, or other electronic information exchanging methods. Data exchanges preferably are conducted over the Internet, LAN, a packet-switched network, WAN, VPN, or other type of packet switched network. One skilled in the pertinent art will appreciate that the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, flash devices and/or any combination thereof. In addition, various signals representing data or events as described herein may be transferred between a source and a destination in the form of electromagnetic waves traveling through signal-conducting media such as metal wires, optical fibers, and/or wireless transmission media—e.g. air and/or space. Data may move between various entities in any of the embodiments of the invention via electronic transmission or manual means. Electronic transmission may utilize email, SMS or any other suitable method. Manual exchange may utilize floppy disks, USB drives, CDs, DVDs or any other suitable mechanism.

An exemplary hardware configuration of a computing system utilized with the invention preferably includes at least one processor or central processing unit (CPU). The CPUs are preferably interconnected via a system bus to a RAM, a ROM, input/output (I/O) adapter, user interface adapter, a communication adapter for connecting the system to a data processing network, the Internet, an Intranet, a LAN, or the like, and a display adapter for connecting the bus to a display device.

Any combination of one or more computer readable medium(s) may be utilized with the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium include an electrical connection having one or more wires, a portable computer diskette, a hard disk, a RAM, a ROM, an erasable programmable read-only memory, an optical fiber, a portable CD-ROM, an optical storage device, a magnetic storage device, or any suitable combination of the foregoing. A computer readable storage medium may be any tangible medium that can contain, or store a program for use by or in connection with a system, apparatus, or device running an instruction.

Computer program code for carrying out operations for aspects of the invention may be written in any combination of one or more programming languages, including an object oriented programming language such as Java, Smalltalk, C++ or the like and conventional procedural programming languages, such as the "C" programming language or similar programming languages. The program code may run entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN or the connection may be made to an external computer through the Internet using an Internet Service Provider.

There are many processing stages for data from DNA (or RNA) sequencing, which can vary depending on the sequencing technology and the application. Processing steps include: Signal processing on electrical measurements from the sequencer; Image processing on optical measurements from the sequencer; Base calling using processed signal or image data to determine the most likely nucleotide sequence and confidence scores; Filtering sequenced reads with low quality or polyclonal clusters; Detecting and trimming adapters, key sequences, barcodes, and low quality read ends; De novo sequence assembly, utilizing De Bruijn graphs and/or sequence graphs; De Bruijn and sequence graph construction, editing, trimming, cleanup, repair, coloring, annotation, comparison, transformation, splitting, splicing, analysis, subgraph selection, traversal, iteration, recursion, searching, filtering, import, export; Mapping reads to a reference genome; Aligning reads to candidate mapping locations in a reference genome; Local assembly of reads mapped to a reference region; Sorting reads by aligned position; Marking duplicate reads, including PCR or optical duplicates; Re-alignment of multiple overlapping reads for indel consistency; Base quality score recalibration; Variant calling (single sample or joint); Structural variant analysis; Copy number variant analysis; Somatic variant calling (tumor sample only, matched tumor/normal, or tumor/unmatched normal); RNA splice junction detection; RNA alternative splicing analysis; RNA transcript assembly; RNA transcript expression analysis; RNA differential expression analysis; RNA variant calling; DNA/RNA difference analysis; DNA methylation analysis and calling; Variant quality score recalibration; Variant filtering; Variant annotation from known variant databases; Sample contamination detection and estimation; Phenotype prediction, disease testing; Treatment response prediction, custom treatment design; Ancestry and mutation history analysis; Population DNA analysis, genetic marker identification; Encoding genomic data into standard formats (e.g. FASTA, FASTQ, SAM, BAM, VCF, BCF); Decoding genomic data from standard formats; Querying, selecting or filtering genomic data subsets; General compression and decompression for genomic files (gzip, BAM compression); Specialized compression and decompression for genomic data (CRAM); Genomic data encryption and decryption; Statistics calculation, comparison, and presentation from genomic data; Genomic result data comparison, accuracy analysis and reporting; Genomic file storage, archival, retrieval, backup, recovery, and transmission; Genomic database construction, querying, access management, data extraction.

A more detailed description of a system for analysis of biological and chemical materials is set forth in van Rooyen et al., U.S. Patent Publication Number 20140371110 for Bioinformatics Systems, Apparatuses, and Methods Executed On An Integrated Circuit Processing Platform, which is hereby incorporated by reference in its entirety. A more detailed description of a system for analysis of biological and chemical materials is set forth in van Rooyen et al., U.S. Patent Publication Number 20140309944 for Bioinformatics Systems, Apparatuses, and Methods Executed On An Integrated Circuit Processing Platform, which is hereby incorporated by reference in its entirety. A more detailed description of a system for analysis of biological and chemical materials is set forth in van Rooyen et al., U.S. Patent Publication Number 20140236490 for Bioinformatics Systems, Apparatuses, and Methods Executed On An Integrated Circuit Processing Platform, which is hereby incorporated by reference in its entirety. A more detailed description of a system for analysis of biological and chemical materials is set forth in van Rooyen et al., U.S. Pat. No. 9,014,989 for Bioinformatics Systems, Apparatuses, and Methods Executed On An Integrated Circuit Processing Platform, which is hereby incorporated by reference in its entirety. A more detailed description of a system for analysis of biological and chemical materials is set forth in U.S. Patent Publication Number 20150339437, for Dynamic Genome Reference Generation For Improved NGS Accuracy And Reproducibility, filed Feb. 24, 2015, which is hereby incorporated by reference in its entirety. A description of a GFET is set forth in Hoffman et al., U.S. patent application Ser. No. 14/963,253, filed on Dec. 9, 2015, for Chemically Sensitive Field Effect Transistor, which is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A method for correlating genome data from a subject with electronic medical record (EMR) data from that subject, the method comprising:

receiving, at a distributed server, via an internet network connection, from an automated sequencer, genomic sequencing data from the subject, the genomic sequencing data comprising a first sequence of nucleotides;

receiving, from a database associated with the distributed server, a reference genome sequence, the reference genome sequence comprising a second sequence of nucleotides;

performing, by the distributed server, a mapping operation whereby the first sequence of nucleotides is mapped to the second sequence of nucleotides to produce mapped results;

performing, by the distributed server, on one or more of the mapped results an alignment operation whereby the mapped result is compared to the reference genome sequence to produce an aligned result performing on the aligned results, by the distributed server, a variant calling operation to produce a genome file, the genome file being specific to the subject and comprising a plurality of variant call files;

indexing and encrypting, by the distributed server, the subject's genome file, the genome file being associated with a first De-identified Identifier (DID) that is unique to the subject;

generating, by the distributed server, an index file for the genome file;

transmitting, via the internet network connection, the index file to a central depository, wherein the index is stored as a plurality of index files;

receiving, at the distributed depository, via the internet network connection, EMR data for the subject, generating, at the distributed depository, a second unique DID for the received EMR data, where the second unique DID corresponds to the first DID; and correlating each genome file of the subject with corresponding EMR data;

wherein an algorithm utilized to generate the DID for each index file is also used for generating the unique DID for the EMR data allowing for matching based on the DID number.

2. The method according to claim 1 wherein the EMR data comprises phenotypic data.

3. The method according to claim 1 wherein the plurality of index files is searchable at a chromosome level, exome level, gene level, allele panel, or at an individual SNP or allele level.

4. The method according to claim 1 wherein each genome file and EMR data is tracked and controlled by an owner of the genome file.

5. The method according to claim 3, further comprising: searching the plurality of index files for a specific anomaly.

6. The method according to claim 1, further comprising: brokering the index file and the matching EMR data.

7. A system for searching correlated genome data and EMR data, the system comprising:

a distributed server, having an internet network connection for receiving from an automated sequencer genomic sequencing data from a subject, the genomic sequencing data comprising a first sequence of nucleotides, the distributed server being associated with a database storing a reference genome sequence, the reference genome sequence comprising a second sequence of nucleotides, and the distributed server being configured for performing each of a mapping operation, an alignment operation, and a variant calling operation on the genomic sequencing data in comparison to the reference genome sequence to produce a genome file, the genome file being specific to the subject and comprising a plurality of variant call files, the distributed server further configured for indexing and encrypting the subject's genome file, the genome file of the subject being associated with a first DID unique to the subject, and generating an index file for the genome file, wherein the index comprises a plurality of index files;

a source for EMR/PHR data comprising a database for encrypting and storing EMR/PHR files of the subject, the encrypted EMR/PHR files having a second DID unique to the subject, the source having an internet network connection for transmitting the encrypted EMR/PHR files, wherein the first DID matches the second DID;

a distributed depository site, associated with both the distributed server and the source for EMR/PHR data via the internet network connection, and configured for receiving the plurality of index files from the distributed server, and for receiving and decrypting the EMR/PHR files from the source, and further configured for associating the plurality of index files with the EMR/PHR files based on their respective DIDs;

a browser for searching one or more of the plurality of index files and the EMR/PHR files;

wherein an algorithm utilized to generate the DID for each index file is also used for generating the unique DID for the EMR/PHR files allowing for matching based on the DID number.

8. The system according to claim 7 wherein the EMR/PHR data comprises phenotypic data.

9. The system according to claim 7 wherein the plurality of index files is searchable at a chromosome level, exome level, gene level, allele panel, or at an individual SNP or allele level.

10. The system according to claim 7 wherein each of the genome file and the EMR/PHR files is capable of being tracked and controlled by the subject.

11. The system according to claim 10 further comprising a privacy control engine configured to allow the subject to control access to the genome file and the EMR/MHR files.

* * * * *